(12) United States Patent
Gysling et al.

(10) Patent No.: US 7,062,976 B2
(45) Date of Patent: Jun. 20, 2006

(54) APPARATUS AND METHOD OF MEASURING GAS VOLUME FRACTION OF A FLUID FLOWING WITHIN A PIPE

(75) Inventors: Daniel L. Gysling, Glastonbury, CT (US); Douglas H. Loose, Southington, CT (US)

(73) Assignee: CiDRA Corporation, Wallingford, CT (US)

( * ) Notice: Subject to any disclaimer, the term of this patent is extended or adjusted under 35 U.S.C. 154(b) by 7 days.

(21) Appl. No.: 10/762,410

(22) Filed: Jan. 21, 2004

(65) Prior Publication Data

US 2004/0210404 A1 Oct. 21, 2004

Related U.S. Application Data

(60) Provisional application No. 60/528,802, filed on Dec. 11, 2003, provisional application No. 60/441,652, filed on Jan. 22, 2003, and provisional application No. 60/441,395, filed on Jan. 21, 2003.

(51) Int. Cl.
*G01F 1/20* (2006.01)

(52) U.S. Cl. .................................. 73/861.18
(58) Field of Classification Search ............ 73/861, 73/861.04, 861.18, 861.25–861.31, 861.42, 73/19.01, 19.03, 19.04, 19.05, 24.01, 24.03, 73/24.04
See application file for complete search history.

(56) References Cited

U.S. PATENT DOCUMENTS

| 4,048,853 A | 9/1977 | Smith et al. ............. 73/861.25 |
| 4,080,837 A | 3/1978 | Alexander et al. ......... 73/61.45 |
| 4,248,085 A | 2/1981 | Coulthard ................ 73/861.06 |

(Continued)

FOREIGN PATENT DOCUMENTS

| WO | WO 93/14382 | 7/1993 |
| WO | WO 99/067629 | 12/1999 |

OTHER PUBLICATIONS

"Noise and Vibration Control Engineering Principles and Applications", Leo L. Beranek and Istvan L. Ver, A. Wiley Interscience Publication, pp. 537–541, Aug. 1992.
"Two Decades of Array Signal Processing Research", The Parametric Approach, H. Krim and M. Viberg, IEEE Signal Processing Magazine, Jul., 1996, pp. 67–94.
"Development of an array of pressure sensors with PVDF film, Experiments in Fluids 26", Jan. 8, 1999, Springer–Verlag.
"Viscous Attenuation of Acoustic Waves in Suspensions" by R.L. Gibson, Jr. and M.N. Toksoz.
U.S. Appl. No. 10/712,833.
U.S. Appl. No. 60/258,802.
U.S. Appl. No. 60/441,652.
U.S. Appl. No. 60/441,395.
"New Flowmeter Principle" by: Walter Boyes –Flow Control Magazine –Oct. 2003.

(Continued)

*Primary Examiner*—Edward Lefkowitz
*Assistant Examiner*—Corey D. Mack

(57) ABSTRACT

An apparatus 10,110 is provided that measures the speed of sound or acoustic disturbances propagating in a fluid or mixture having entrained gas/air to determine the gas volume fraction of the flow 12 propagating through a pipe 14. The apparatus includes an array of pressure sensors disposed axially along the length of the pipe. The apparatus measures the speed of sound propagating through the fluid to determine the gas volume fraction of the mixture using adaptive array processing techniques to define an acoustic ridge in the k-ω plane. The slope of the acoustic ridge 61 defines the speed of sound propagating through the fluid in the pipe.

20 Claims, 6 Drawing Sheets

U.S. PATENT DOCUMENTS

| | | | | |
|---|---|---|---|---|
| 4,445,389 A | 5/1984 | Potzick et al. | ............ | 73/861.27 |
| 4,896,540 A | 1/1990 | Shakkottai et al. | ...... | 73/861.02 |
| 5,040,415 A | 8/1991 | Barkhoudarian | ......... | 73/861.03 |
| 5,083,452 A | 1/1992 | Hope | ......................... | 73/61 R |
| 5,218,197 A | 6/1993 | Carroll | .................. | 250/227.19 |
| 5,285,675 A | 2/1994 | Colgate et al. | .............. | 73/23.2 |
| 5,367,911 A | 11/1994 | Jewell et al. | ............ | 73/861.08 |
| 5,398,542 A | 3/1995 | Vasbinder | .................... | 73/40.5 |
| 5,524,475 A | 6/1996 | Kolpak et al. | ............ | 73/19.03 |
| 5,526,844 A | 6/1996 | Kamen et al. | ......... | 137/614.11 |
| 5,591,922 A | 1/1997 | Segeral et al. | ............ | 73/861.04 |
| 5,741,980 A | 4/1998 | Hill et al. | ................ | 73/861.04 |
| 5,770,805 A | 6/1998 | Castel | ..................... | 73/861.04 |
| 5,770,806 A | 6/1998 | Hiismaki | ................. | 73/861.29 |
| 5,835,884 A | 11/1998 | Brown | ..................... | 73/861.04 |
| 5,845,033 A | 12/1998 | Berthold et al. | .............. | 385/12 |
| 5,948,959 A | 9/1999 | Peloquin | ......................... | 73/1.83 |
| 6,016,702 A | 1/2000 | Maron | ......................... | 73/705 |
| 6,151,958 A | 11/2000 | Letton et al. | ............. | 73/61.79 |
| 6,202,494 B1 | 3/2001 | Ricbel et al. | ............ | 73/861.29 |
| 6,209,388 B1 * | 4/2001 | Letton et al. | .............. | 73/61.79 |
| 6,354,147 B1 | 3/2002 | Gysling et al. | ............ | 73/61.79 |
| 6,378,357 B1 | 4/2002 | Han et al. | .................. | 73/54.41 |
| 6,435,030 B1 | 8/2002 | Gysling et al. | ................ | 73/587 |
| 6,443,226 B1 | 9/2002 | Diener et al. | ............. | 166/241.6 |
| 6,450,037 B1 | 9/2002 | McGuinn et al. | .......... | 73/61.79 |
| 6,463,813 B1 | 10/2002 | Gysling | .................. | 73/862.59 |
| 6,536,291 B1 | 3/2003 | Gysling et al. | .......... | 73/861.42 |
| 6,550,342 B1 | 4/2003 | Croteau et al. | ................ | 73/800 |
| 6,558,036 B1 | 5/2003 | Gysling et al. | ............. | 374/147 |
| 6,587,798 B1 | 7/2003 | Kersey et al. | ................ | 702/50 |
| 6,601,458 B1 | 8/2003 | Gysling et al. | .......... | 73/861.04 |
| 6,609,069 B1 | 8/2003 | Gysling | ........................ | 702/48 |
| 6,691,584 B1 | 2/2004 | Gysling et al. | .......... | 73/861.42 |
| 6,698,297 B1 | 3/2004 | Gysling | .................... | 73/861.63 |
| 6,732,575 B1 | 5/2004 | Gysling et al. | ............. | 73/61.79 |
| 6,776,054 B1 * | 8/2004 | Stephenson et al. | ...... | 73/861.63 |
| 6,782,150 B1 | 8/2004 | Davis et al. | ................... | 385/12 |
| 6,813,962 B1 | 11/2004 | Gysling et al. | .......... | 73/861.26 |
| 6,837,098 B1 | 1/2005 | Gysling et al. | ............. | 73/61.79 |
| 6,862,920 B1 | 3/2005 | Gysling et al. | ............. | 73/61.79 |
| 6,868,737 B1 | 3/2005 | Croteau et al. | ................ | 73/800 |
| 6,889,562 B1 | 5/2005 | Gysling et al. | .......... | 73/861.42 |
| 6,898,541 B1 | 5/2005 | Gysling et al. | ............. | 702/100 |
| 2002/0123852 A1 | 9/2002 | Gysling et al. | | |
| 2002/0129662 A1 | 9/2002 | Gysling et al. | | |
| 2003/0038231 A1 | 2/2003 | Bryant et al. | | |
| 2003/0089161 A1 | 5/2003 | Gysling | | |
| 2003/0136186 A1 | 7/2003 | Gysling et al. | | |
| 2004/0167735 A1 | 8/2004 | Rothman | | |
| 2004/0199340 A1 | 10/2004 | Kersey et al. | | |
| 2004/0226386 A1 | 11/2004 | Gysling et al. | | |

OTHER PUBLICATIONS

"Sonar gets into flow" by: Daniel L. Gysling and Douglas H. Loose –Jan. 2004.

"Sonar–Based Volumetric Flow Meter for Pulp and Paper Applications" by: David L. Gysling and Douglas H. Loose –Dec. 3, 2002.

37 Sonar–Based Volumetric Flow Meter for Chemical and Petrochemical Applications by: Daniel L. Gysling and Douglas H. Loose –Feb. 14, 2003.

* cited by examiner

APPARATUS AND METHOD OF MEASURING GAS VOLUME FRACTION OF A FLUID FLOWING WITHIN A PIPE

CROSS-REFERENCE TO RELATED PATENT APPLICATIONS

This application claims the benefit of U.S. Provisional Patent Application No. 60/528,802 filed Dec. 11, 2003, U.S. Provisional Patent Application No. 60/441,652 filed Jan. 22, 2003, U.S. Provisional Patent Application No. 60/441,395 filed Jan. 21, 2003, which are all incorporated herein by reference.

TECHNICAL FIELD

This invention relates to an apparatus for measuring a flow having entrained gas therein, and more particularly to an apparatus that measures the speed of sound propagating through the flow to determine the gas volume fraction of the gas in the process.

BACKGROUND ART

The present invention provides an apparatus and method of measuring gas volume fraction in a process flow or fluid, such as slurries used in the paper and pulp industries and in other industries. Slurries commonly used in the paper and pulp industry are mostly water and typically contain between 1% and 10% pulp content by mass. Monitoring the gas volume fraction of a slurry can lead to improved quality and efficiency of the paper production process.

Processes run in the paper and pulp industry can often, either intentionally or unintentionally, entrain gas/air. Typically, this entrained air results in measurement errors in process monitoring equipment such as volumetric flow measurements and consistency meters.

Industry estimates indicate that entrained air levels of 2–4% are common. Since most process flow monitors are unable to distinguish between air and liquid, interpreting their output as liquid flow rates would result in a overestimate of the liquid by the volumetric flow rate of the air present at the measurement location. Similarly, for the void fraction of the air within the pipe can cause errors in consistency measurements.

Thus, providing a method and apparatus for measuring entrained air in paper and pulp slurries, for example, would provide several benefits. Firstly, it would provide a means to screen the output of process instrumentation. Secondly, in addition to screening the measurements, an accurate measurement of the entrained air would provide a means to correct the output of volumetric flow meters and consistency meters. Thirdly, monitoring variations in the amount of entrained air in a given process could be indicative of process anomalies, such a worn bushing or cavitating pumps and/or valves.

Multiphase process flow rate is a critical process control parameter for the paper and pulp industry. Knowing the amounts of liquid, solids and entrained gases flowing in process lines is key to optimizing the overall the papermaking process. Unfortunately, significant challenges remain in the achieving accurate, reliable, and economical monitoring of multiphase flow rates of paper and pulp slurries. Reliability challenges arise due the corrosive and erosive properties of the slurry. Accuracy challenges stem from the multiphase nature of the slurries. Economical challenges arise from the need to reduce total lifetime cost of flow measurement, considering installation and maintenance costs in addition to the initial cost of the equipment.

Currently, there is an unmet need for multiphase flow measurement in the processing industry, such as the paper and pulp industry. Real time flow measurement is typical restricted to monitoring the total volumetric flow rate in a process line without providing information on the composition of the process mixture. For example, electromagnetic flow meters are the most widely used flow meters in the paper and pulp industry, however they provide no indication of presence of entrained air, with its presence resulting in an over prediction of the volumetric flow of process fluid by the amount of air entrained. Consistency meter provide a measurement of the percentage of solids within the process, however this technology remains more of an art than a science. Furthermore, although entrained air is known to have a large, often deleterious, impact on the paper making process, instrumentation is currently not available to provide this measurement on a real time basis.

In one embodiment of the present invention, the apparatus and method improves the determination of consistency of paper and pulp slurries. Consistency refers to the mass fraction of pulp contained in water and pulp slurries used in the paper making process. Consistency measurements are critical in the optimization of the paper making process. Currently, many companies produce consistency meters employing various technology to serve the paper and pulp industry. Unfortunately, accurate and reliable measurement of consistency remains an elusive objective. Typically, interpreting the output of a consistency meter in terms of actual consistency is more of an art than a science.

Of the various types of consistency meters on the market, microwave based meters may represent the best the solution for many applications. One such microwave-based consistency meter is manufactured by Toshiba. Microwave consistency meters essentially measure speed or velocity the microwave signal propagates through the medium being measured. For example, the speed of the microwave signal through water is approximately 0.1 time the speed of light in a vacuum (c), through air is approximately 1.0 times the speed of light in a vacuum, and through fiber (or pulp) is approximately 0.6 times the speed of light in a vacuum.

The velocity of the microwave signal propagating through the paper pulp slurry is measure by the conductive effects of the slurry, in accordance with the following equation:

$$V = c * sqrt(E)$$

Where V is the velocity of the microwave signal propagating through the slurry, c is the speed of light in a vacuum, and E is the relative conductivity of the material. Typical values of relative conductivity for material comprising a paper/pulp slurry, for example, are:

Water relative conductivity=80;

Air relative conductivity=1; and

Fiber relative conductivity=3.

These meters typically work well in the absence of entrained air. With entrained air present, the air displaces water and looks like additional pulp fiber to the microwave meter. Thus, uncertainty in the amount of entrained air translates directly into uncertainty in consistency.

SUMMARY OF THE INVENTION

Objects of the present invention include an apparatus having a device for determining the speed of sound propagating within a pipe to determine the gas volume fraction of a process fluid or flow flowing within a pipe.

According to the present invention, an apparatus for measuring the gas volume fraction process flow flowing within a pipe is provided. The apparatus includes at least one sensor for providing a sound measurement signal indicative of the speed of sound propagating within the pipe. A processor determines the gas volume fraction of the flow, in response to the sound measurement signal.

According to the present invention, a method of measuring the gas volume fraction process flow flowing within a pipe comprises measuring the speed of sound propagating within the pipe, and determining the gas volume fraction of the flow, in response to the measured speed of sound.

The foregoing and other objects, features and advantages of the present invention will become more apparent in light of the following detailed description of exemplary embodiments thereof.

BEST MODE FOR CARRYING OUT THE INVENTION

Figure 1:
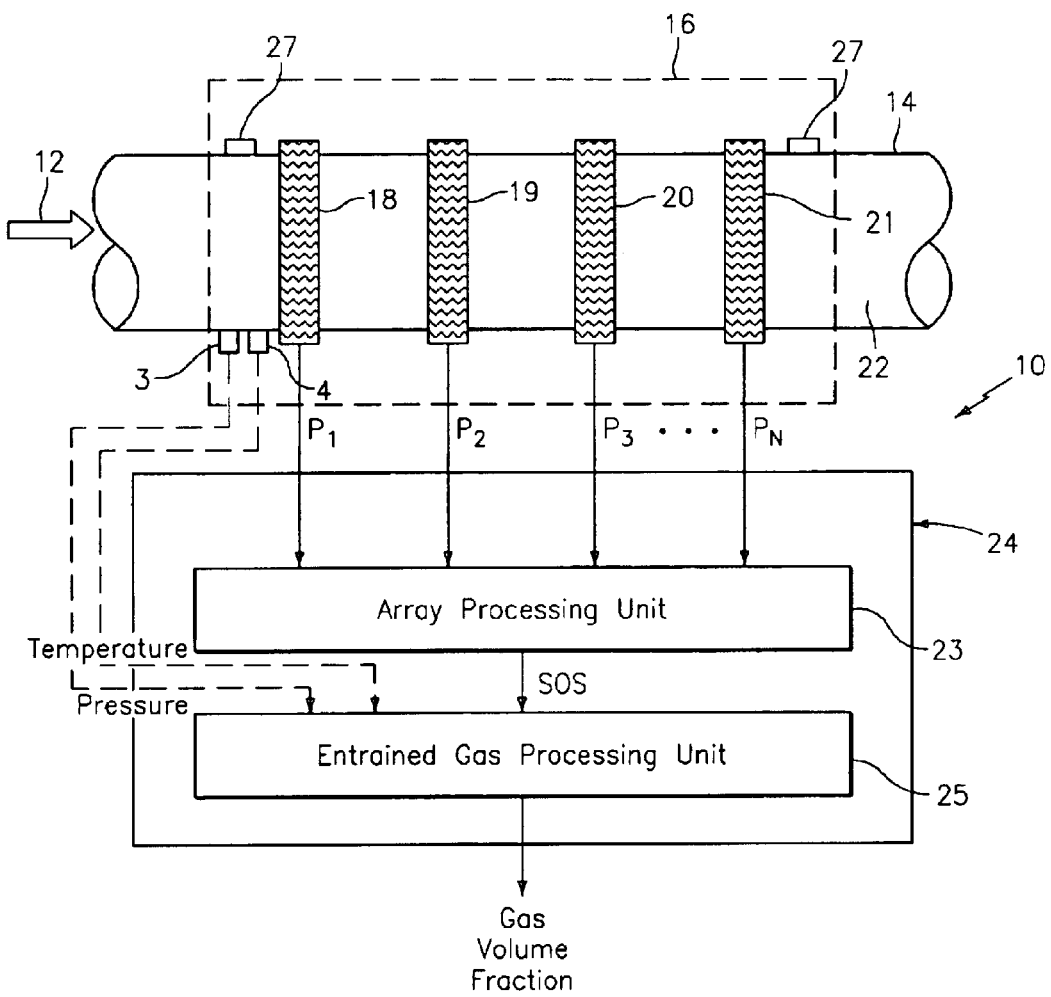
FIG. 1 is a schematic illustration of an apparatus having an array of sensors onto a pipe for measuring the volumetric flow and gas volume fraction of the mixture flowing in the pipe having entrained gas/air therein, in accordance with the present invention.

Referring to FIG. 1, an apparatus, generally shown as 10, is provided to measure gas volume fraction in liquids and mixtures (e.g. paper and pulp slurries or other solid liquid mixtures) having entrained gas therein (including air). The apparatus 10 in accordance with the present invention determines the speed at which sound propagates through the fluid 12 within a pipe 14 to measure entrained gas in liquids and/or mixtures 12. To simplify the explanation of the present invention, the flow 12 propagating through the pipe will be referred to as a mixture or slurry with the understanding that the flow may be a liquid or any other mixture having entrained gas therein.

The following approach may be used with any technique that measures the sound speed of a flow or speed at which sound propagates through the flow 12. However, it is particularly synergistic with flow meters using sonar-based array processing, such as described in U.S. patent application Ser. No. 10/007,736 and U.S. patent application Ser. No. 09/729,994, filed Dec. 4, 200, now U.S. Pat. No. 6,609,069, which are incorporated herein by reference. While the sonar-based flow meter using an array of sensors to measure the speed of sound of an acoustic wave propagating through the mixture is shown and described, one will appreciate that any means for measuring the speed of sound of the acoustic wave may used to determine the entrained gas volume fraction of the mixture/fluid.

Figure 2:
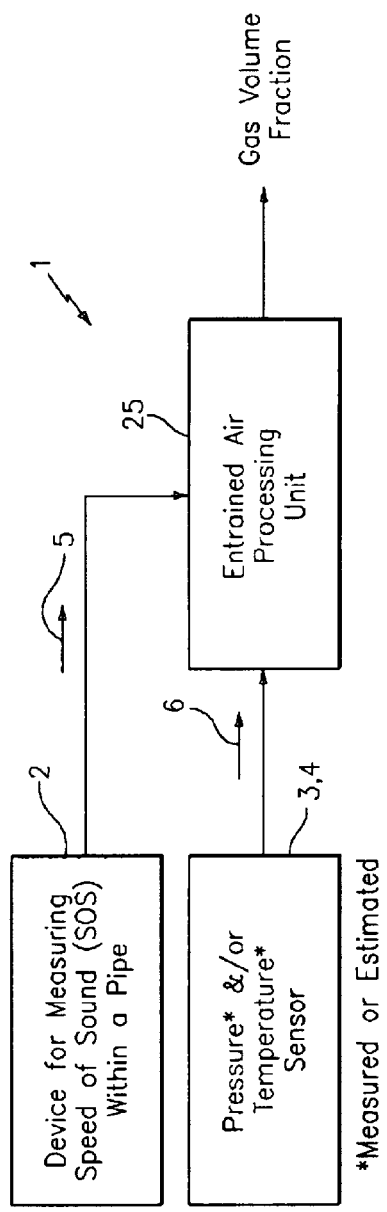
FIG. 2 is a block diagram of an embodiment of the apparatus of FIG. 1, in accordance with the present invention.

FIG. 2 is a block diagram 1 of the apparatus 10 of FIG. 1 that includes a device 2 for measuring the speed of sound (SOS) propagating through the flow 12 within a pipe 14. A pressure sensor and/or temperature sensor 3,4 measures the pressure and/or temperature, respectively, of the mixture 12 flowing through the pipe. In response to the speed of sound signal 5 and the characteristics 6 of the flow (e.g., pressure and temperature), an entrained gas processing unit 25 determines the gas volume fraction (GVF) of the flow 12. The pressure and temperature sensors enables the apparatus 10 to compensate or determine the gas volume fraction for dynamic changes in the pressure and temperature of the flow 12. Alternatively, the pressure and/or temperature may be estimated rather than actually measured.

Figure 3:
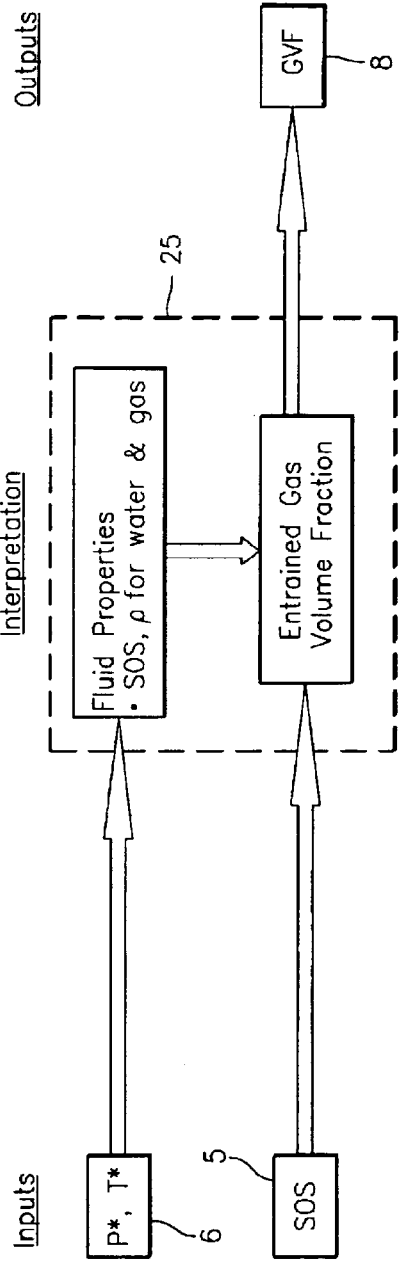
FIG. 3 is a functional flow diagram of an apparatus embodying the present invention that compensates the volumetric flow measurement of a volumetric flow meter, in accordance with the present invention.

A flow chart 13 shown in FIG. 3 illustrates the function of the entrained gas processing unit 25. As shown in FIG. 2, the inputs to the processing unit 25 includes the speed of sound (SOS) 5 within the mixture 12 in the pipe 14, and the pressure and/or temperature of the mixture. The fluid properties of the mixture (e.g., SOS and density) are determined knowing the pressure and temperature of the mixture. The gas volume fraction of the mixture (GVF) is determined using the SOS measurement and fluid properties, which will be described in greater detail hereinafter.

Other information relating to the gas volume fraction in a fluid and the speed of sound (or sonic velocity) in the fluid, is described in "Fluid Mechanics and Measurements in two-phase flow Systems", Institution of mechanical engineers, proceedings 1969–1970 Vol. 184 part 3C, September 24–25, 1969, Birdcage Walk, Westminster, London S.W. 1, England, which is incorporated herein by reference.

FIG. 1 illustrates a schematic drawing of one embodiment of the present invention. The apparatus 10 includes a sensing device 16 comprising an array of pressure sensors (or transducers) 18–21 spaced axially along the outer surface 22 of a pipe 14, having a process flow propagating therein. The pressure sensors measure the unsteady pressures produced by acoustical disturbances within the pipe, which are indicative of the SOS propagating through the mixture 12. The output signals ($P_1$–$P_N$) of the pressure sensors 18–21 are provided to the processor 24, which processes the pressure measurement data and determines the speed of sound and gas volume fraction (GVF).

In an embodiment of the present invention shown in FIG. 1, the apparatus 10 has at least pressure sensors 18–21 disposed axially along the pipe 14 for measuring the unsteady pressure $P_1$–$P_N$ of the mixture 12 flowing therethrough. The speed of sound propagating through the flow 12 is derived by interpreting the unsteady pressure field within the process piping 14 using multiple transducers displaced axially over ~2 diameters in length. The flow measurements can be performed using ported pressure transducers or clamp-on, strain-based sensors.

The apparatus 10 has the ability to measure the gas volume fraction by determining the speed of sound of acoustical disturbances or sound waves propagating through the flow 12 using the array of pressure sensors 18–21. While the apparatus of FIG. 1 shows at least four pressure sensors 18–21, the present invention contemplates an apparatus having an array of two or more pressure sensors and having as many as sixteen (16) pressure sensors.

Generally, the apparatus 10 measures unsteady pressures created by acoustical disturbances propagating through the flow 12 to determine the speed of sound (SOS) propagating through the flow. Knowing the pressure and/or temperature of the flow and the speed of sound of the acoustical disturbances, the processing unit 24 can determine the gas volume fraction of the mixture, as described and shown in FIG. 3.

The apparatus in FIG. 1 also contemplates providing one or more acoustic sources 27 to enable the measurement of the speed of sound propagating through the flow for instances of acoustically quiet flow. The acoustic source may be a device the taps or vibrates on the wall of the pipe, for example. The acoustic sources may be disposed at the input end of output end of the array of sensors 18–21, or at both ends as shown. One should appreciate that in most instances the acoustics sources are not necessary and the apparatus passively detects the acoustic ridge provided in the flow 12. The passive noise includes noise generated by pumps, valves, motors, and the turbulent mixture itself.

Figure 4:
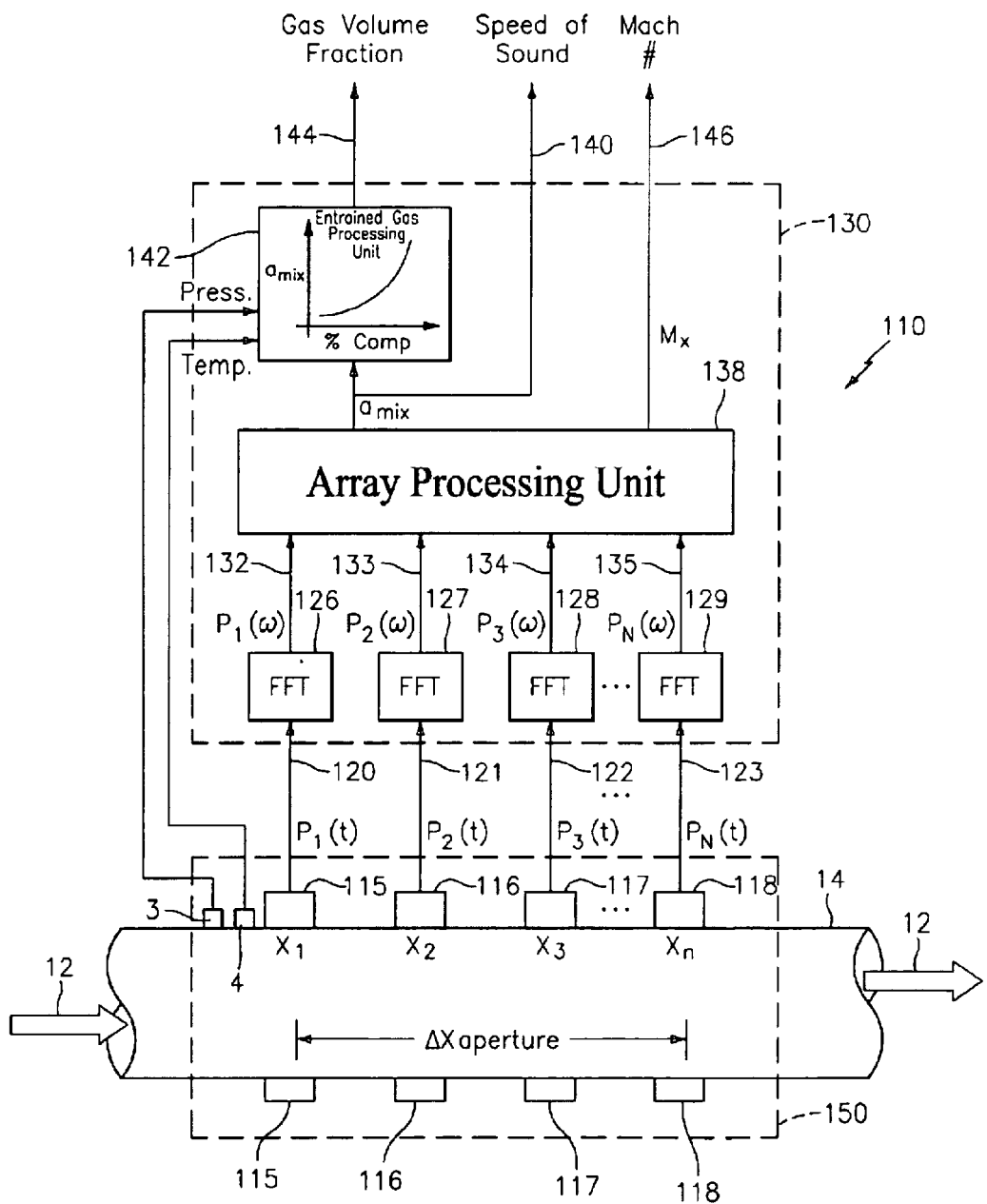
FIG. 4 is a block diagram of an apparatus for measuring the speed of sound propagating through a process flow flowing within a pipe, in accordance with the present invention.

The apparatus 10 of the present invention may be configured and programmed to measure and process the detected unsteady pressures $P_1(t)$–$P_N(t)$ created by acoustic waves propagating through the mixture to determine the SOS through the flow 12 in the pipe 14. One such apparatus 110 is shown in FIG. 4 that measures the speed of sound (SOS) of one-dimensional sound waves propagating through the mixture to determine the gas volume fraction of the mixture. It is known that sound propagates through various mediums at various speeds in such fields as SONAR and RADAR fields. The speed of sound propagating through the pipe and mixture 12 may be determined using a number of known techniques, such as those set forth in U.S. patent application Ser. No. 09/344,094, entitled "Fluid Parameter Measurement in Pipes Using Acoustic Pressures", filed Jun. 25, 1999, now U.S. Pat. No. 6,354,147; U.S. patent application Ser. No. 09/729,994, filed Dec. 4, 2002, now U.S. Pat. No. 6,609,069; U.S. patent application Ser. No. 09/997,221, filed Nov. 28, 2001, now U.S. Pat. No. 6,587,798; and U.S. patent application Ser. No. 10/007,749, entitled "Fluid Parameter Measurement in Pipes Using Acoustic Pressures", filed Nov. 7, 2001, each of which are incorporated herein by reference.

In accordance with one embodiment of the present invention, the speed of sound propagating through the mixture 12 is measured by passively listening to the flow with an array of unsteady pressure sensors to determine the speed at which one-dimensional compression waves propagate through the mixture 12 contained within the pipe 14.

As shown in FIG. 4, an apparatus 110 embodying the present invention has an array of at least three acoustic pressure sensors 115,116,117, located at three locations $x_1,x_2,x_3$ axially along the pipe 14. One will appreciate that the sensor array may include more than three pressure sensors as depicted by pressure sensor 118 at location $x_N$. The pressure generated by the acoustic waves may be measured through pressure sensors 115–118. The pressure sensors 15–18 provide pressure time-varying signals $P_1(t)$, $P_2(t),P_3(t),P_N(t)$ on lines 120,121,122,123 to a signal processing unit 130 to known Fast Fourier Transform (FFT) logics 126,127,128,129, respectively. The FFT logics 126–129 calculate the Fourier transform of the time-based input signals $P_1(t)$–$P_N(t)$ and provide complex frequency domain (or frequency based) signals $P_1(\omega),P_2(\omega),P_3(\omega),P_N(\omega)$ on lines 132,133,134,135 indicative of the frequency content of the input signals. Instead of FFT's, any other technique for obtaining the frequency domain characteristics of the signals $P_1(t)$–$P_N(t)$, may be used. For example, the cross-spectral density and the power spectral density may be used to form a frequency domain transfer functions (or frequency response or ratios) discussed hereinafter.

The frequency signals $P_1(\omega)$–$P_N(\omega)$ are fed to an array processing unit 138 which provides a signal to line 40 indicative of the speed of sound of the mixture $a_{mix}$, discussed more hereinafter. The $a_{mix}$ signal is provided to an entrained gas processing unit 142, similar to the processing unit 25, which converts $a_{mix}$ to a percent composition of a mixture and provides a gas volume fraction or % Comp signal to line 44 indicative thereof (as discussed hereinafter).

The data from the array of sensors 115–118 may be processed in any domain, including the frequency/spatial domain, the temporal/spatial domain, the temporal/wave-number domain or the wave-number/frequency (k-$\omega$) domain. As such, any known array processing technique in any of these or other related domains may be used if desired, similar to the techniques used in the fields of SONAR and RADAR.

Figure 9:
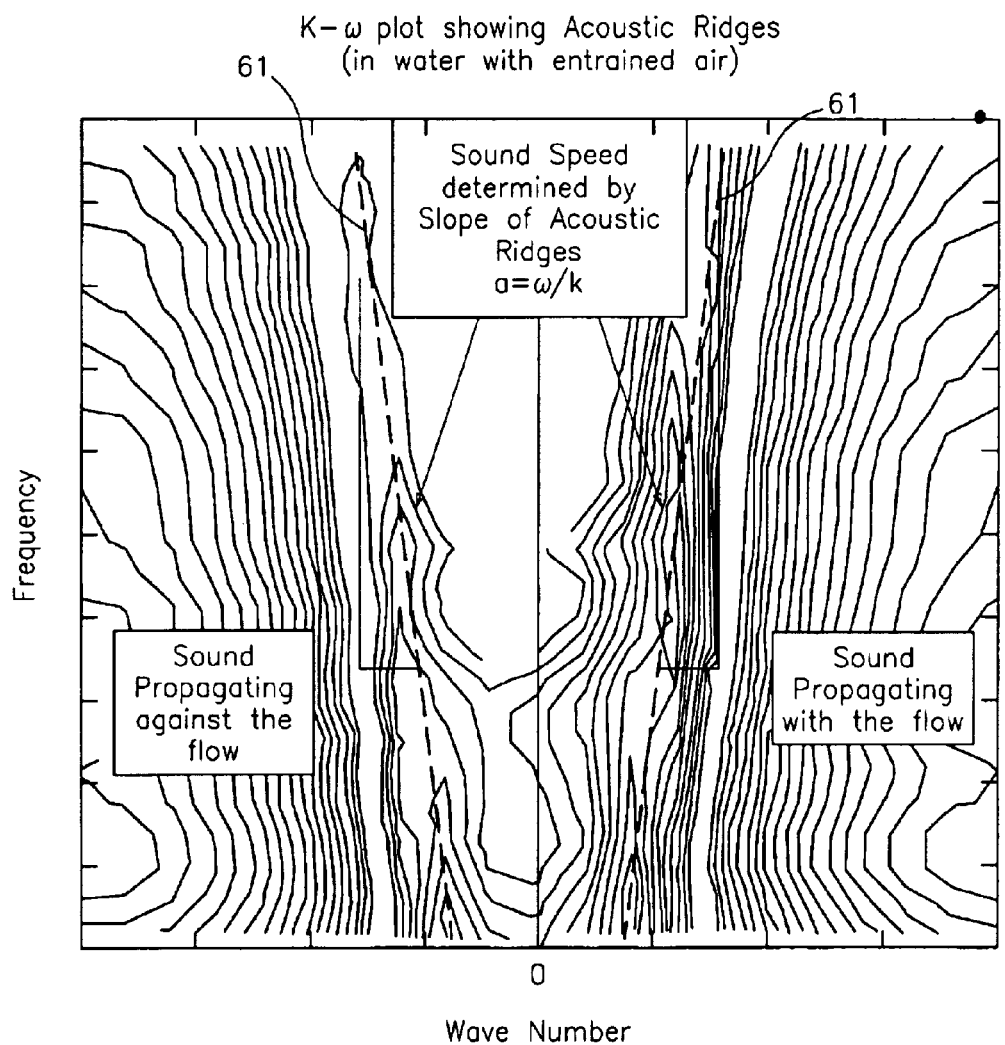
FIG. 9 is a K-w plot for acoustic field within 3 inch pipe containing ~2% air by volume entrained in water flowing 240 gpm, in accordance with the present invention.

One such technique of determining the speed of sound propagating through the flow 12 is using array processing techniques to define an acoustic ridge in the k-$\omega$ plane as shown in FIG. 9. The slope of the acoustic ridge is indicative of the speed of sound propagating through the flow 12. This technique is similar to that described in U.S. Pat. No. 6,587,798 filed Nov. 28, 2001, titled "Method and System for Determining The Speed of Sound in a Fluid Within a Conduit", which is incorporated herein by reference. The speed of sound (SOS) is determined by applying sonar arraying processing techniques to determine the speed at which the one dimensional acoustic waves propagate past the axial array of unsteady pressure measurements distributed along the pipe 14.

The signal processor 24 performs a Fast Fourier Transform (FFT) of the time-based pressure signals $P_1(t)$–$P_N(t)$ to convert the pressure signal into the frequency domain. The power of the frequency-domain pressure signals are then determined and defined in the k-$\omega$ plane by using array processing algorithms (such as Capon and Music algorithms). The acoustic ridge in the k-$\omega$ plane, as shown in the k-$\omega$ plot of FIG. 9, is then determined. The speed of sound (SOS) is determined by measuring slope of the acoustic ridge. The gas volume fraction is then calculated or otherwise determined, as described hereinafter.

The flow meter of the present invention uses known array processing techniques, in particular the Minimum Variance, Distortionless Response (MVDR, or Capon technique), to identify pressure fluctuations, which convect with the materials flowing in a conduit and accurately ascertain the velocity, and thus the flow rate, of said material. These processing techniques utilize the covariance between multiple sensors 18–21 at a plurality of frequencies to identify signals that behave according to a given assumed model; in the case of the apparatus 10, a model, which represents pressure variations 20 convecting at a constant speed across the pressure sensors comprising the flow meter monitoring head 12.

To calculate the power in the k-ω plane, as represent by a k-ω plot (see FIG. 9) of either the pressure signals, the processor 58 determines the wavelength and so the (spatial) wavenumber k, and also the (temporal) frequency and so the angular frequency ω, of various spectral components of the acoustic waves created passively or actively within the pipe. There are numerous algorithms available in the public domain to perform the spatial/temporal decomposition of arrays of sensor units 18–21.

In the case of suitable acoustic pressures being present, the power in the k-ω plane shown in a k-ω plot of FIG. 9 so determined will exhibit a structure that is called an acoustic ridge 61 associated with sound propagating with the flow and one associated with sound propagating against the flow. The acoustic ridge represents the concentration of the disturbances that propagate with and against the flow and is a mathematical manifestation of the relationship between the spatial variations and temporal variations described above. Such a plot will indicate a tendency for k-ω pairs to appear more or less along a line with some slope, the slope indicating the speed of sound traveling in both directions, as is described in more detail below. The power in the k-ω plane so determined is then provided to a acoustic ridge identifier, which uses one or another feature extraction method to determine the location and orientation (slope) of any acoustic ridge present in the k-ω plane. Finally, information including the acoustic ridge orientation (slope) is used by an analyzer to determine the speed of sound.

The array processing unit 23 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by k=2π/λ where λ is the wavelength of a spectral component, and corresponding angular frequencies given by ω=2πν.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine speed of sound propagating through the fluid 12.

Also, some or all of the functions within the processor 130 may be implemented in software (using a microprocessor or computer) and/or firmware, or may be implemented using analog and/or digital hardware, having sufficient memory, interfaces, and capacity to perform the functions described herein.

It is within the scope of the present invention that the pressure sensor spacing may be known or arbitrary and that as few as two sensors are required if certain information is known about the acoustic properties of the process flow 12. The pressure sensors are spaced sufficiently such that the entire length of the array (aperture) is at least a significant fraction of the measured wavelength of the acoustic waves being measured. The acoustic wavelength is a function of the type or characteristics of flow 12.

Based on the above discussion, one may use a short length scale aperture to measure the sound speed. For example, the characteristic acoustic length scale is: λ=c/f; where c is the speed of sound in a mixture, f is frequency and λ is wavelength.

If Aperture=L and if L/λ is approx. constant.

Then Lwater/λwater=Lwater*f/$C_{water}$≈$L_{GVF}$*f/$c_{GVF}$

Therefore: $L_{GVF}$=Lwater ($C_{GVF}$/$C_{water}$); where GVF is gas volume fraction.

Thus for SOS of water (Cwater=5,000 ft/sec), and SOS of the Gas volume fraction (C GVF=500 ft/sec) and a length aperture of L water=5 ft (which we have shown is sufficient to accurately measure the SOS of water), the length aperture for a gas volume fraction $L_{GVF}$ would be about 0.5 feet.

The entrained gas processing unit 25 assumes a nearly isothermal condition for the flow 12. As such the gas volume fraction or the void fraction is related to the speed of sound by the following quadratic equation:

$$Ax^2+Bx+C=0$$

wherein x is the speed of sound, A=1+rg/rl*($K_{eff}$/P−1)−$K_{eff}$/P, B=$K_{eff}$/P−2+rg/rl; C=1−$K_{eff}$/rl*$a_{meas}^2$); Rg=gas density, rl=liquid density, $K_{eff}$=effective K (modulus of the liquid and pipewall), P=pressure, and $a_{meas}$=measured speed of sound.

Effectively,

Gas Voulume Fraction (GVF)=(−B+sqrt(B^2−4*A*C))/(2*A)

Alternatively, the sound speed of a mixture can be related to volumetric phase fraction ($\phi_i$) of the components and the sound speed (a) and densities (ρ) of the component through the Wood equation.

$$\frac{1}{\rho_{mix} a_{mix\infty}^2} = \sum_{i=1}^{N} \frac{\phi_i}{\rho_i a_i^2} \quad \text{where } \rho_{mix} = \sum_{i=1}^{N} \rho_i \phi_i$$

One dimensional compression waves propagating within a mixture 12 contained within a pipe 14 exert an unsteady internal pressure loading on the pipe. The degree to which the pipe displaces as a result of the unsteady pressure loading influences the speed of propagation of the compression wave. The relationship among the infinite domain speed of sound and density of a mixture; the elastic modulus (E), thickness (t), and radius (R) of a vacuum-backed cylindrical conduit; and the effective propagation velocity ($a_{eff}$) for one dimensional compression is given by the following expression:

$$a_{eff} = \frac{1}{\sqrt{\frac{1}{a_{mix\infty}^2} + \rho_{mix} \frac{2R}{Et}}} \quad (\text{eq 1})$$

Note: "vacuum backed" as used herein refers to a situation in which the fluid surrounding the pipe externally has negligible acoustic impedance compared to that of the mixture internal to the pipe 14. For example, meter containing a typical water and pulp slurry immersed in air at standard atmospheric conditions satisfies this condition and can be considered "vacuum-backed".

Figure 5:
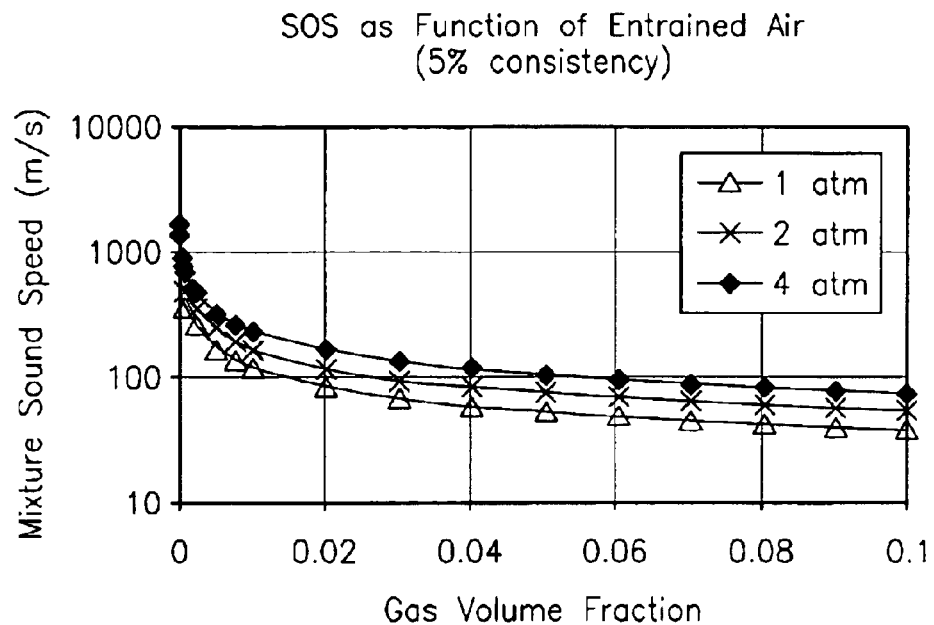
FIG. 5 is a plot of Mixture Sound Speed as a function of gas volume fraction for a 5% consistency slurry over a range of process pressures, in accordance with the present invention.

The mixing rule essentially states that the compressibility of a mixture (1/(ρa²)) is the volumetrically-weighted average of the compressibilities of the components. For gas/liquid mixtures 12 at pressure and temperatures typical of paper and pulp industry, the compressibility of gas phase is orders of magnitudes greater than that of the liquid. Thus, the compressibility of the gas phase and the density of the liquid phase primarily determine mixture sound speed, and as such, it is necessary to have a good estimate of process pressure to interpret mixture sound speed in terms of volumetric fraction of entrained gas. The effect of process pressure on the relationship between sound speed and entrained air volume fraction is shown in FIG. 5.

Figure 6:
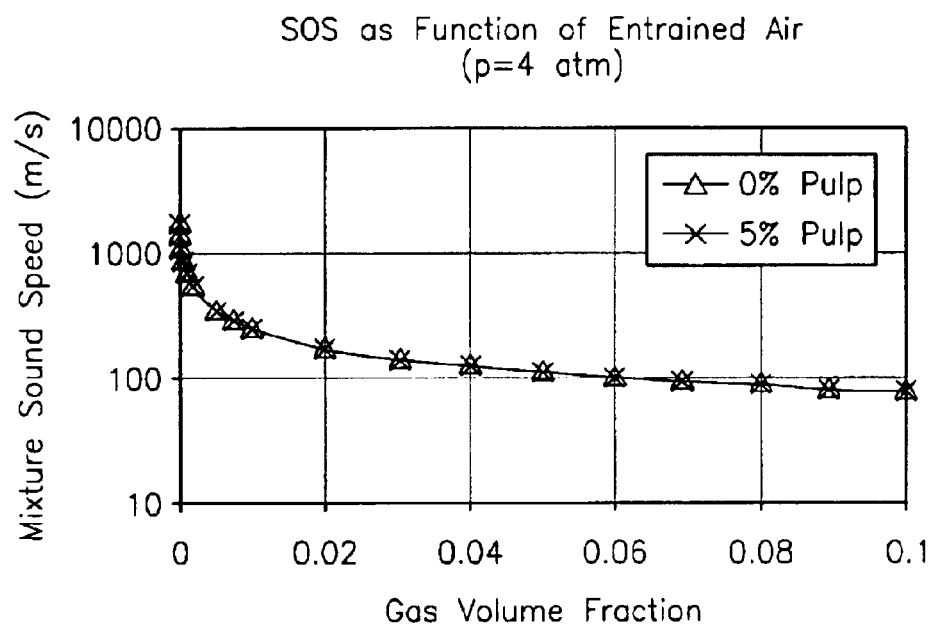
FIG. 6 is a plot of Mixture Sound Speed a function of gas volume fraction for pure water and a 5% consistency slurry at 4 atm process pressure, in accordance with the present invention.

Conversely, however, detailed knowledge of the liquid/slurry is not required for entrained air measurement. Variations in liquid density and compressibility with changes in consistency have a negligible effect on mixture sound speed compared to the presence of entrained air. FIG. 6 shows the mixture sound speed as a function of entrained air volume fraction for two slurries, one with 0% wood fiber and the other with 5% wood fiber by volume. As shown, the relationship between mixture sound speed and gas volume fraction is essentially indistinguishable for the two slurries. Furthermore, mixture sound speed is shown to an excellent indicator of gas volume fraction, especially for the trace to moderate amounts of entrained air, from 0 to 5% by volume, typically encountered in the paper and pulp industry.

For paper and pulp slurries, the conditions are such that for slurries with non-negligible amounts of entrained gas, say <0.01%, the compliance of standard industrial piping (Schedule 10 or 40 steel pipe) is typically negligible compared to that of the entrained air.

Figure 7:
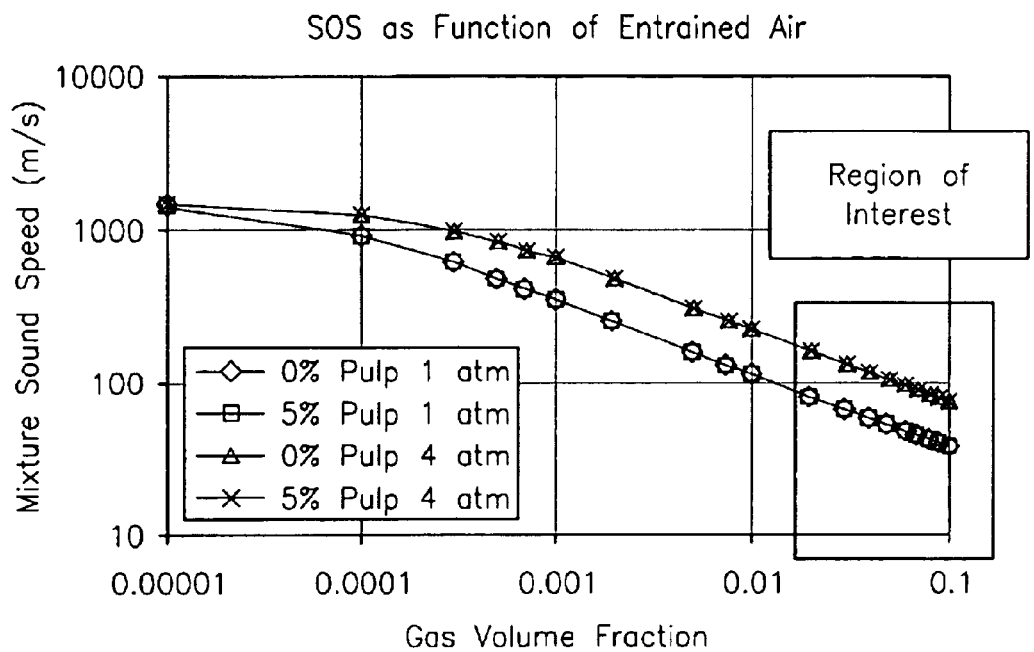
FIG. 7 is a plot of Mixture Sound Speed as a function of gas volume fraction for different consistency slurry over a range of process pressures, in accordance with the present invention.
Figure 8:
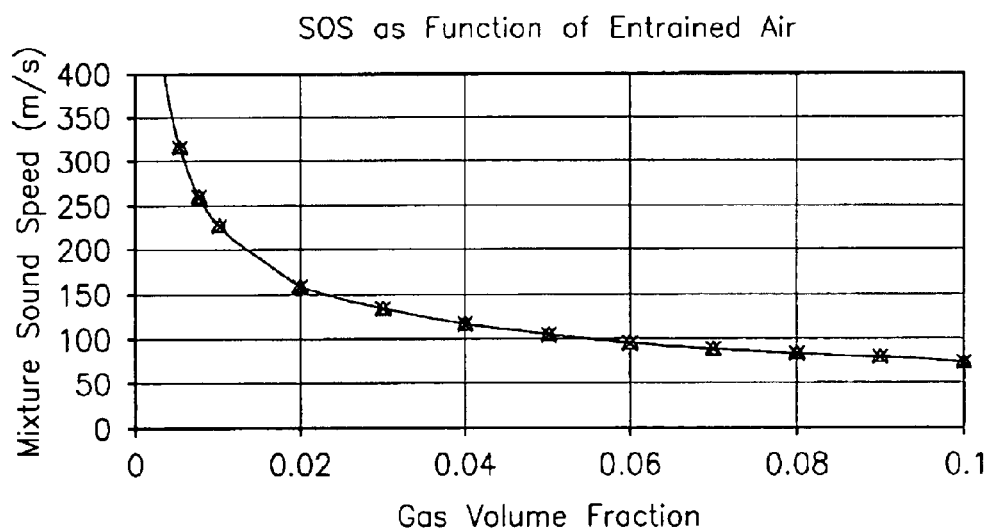
FIG. 8 is a plot of Mixture Sound Speed a function of entrained air volume fraction for slurry at a process pressure, in accordance with the present invention.

FIGS. 7 and 8 above show the relationship between sound speed and entrained air for slurries 12 with pulp contents representative of the range used in the paper and pulp industry. Referring to FIG. 7, two slurry consistencies are shown; representing the lower limit, a pure water mixture is considered, and representing the higher end of consistencies, a 5% pulp/95% water slurry is considered. Since the effect of entrained air on the sound speed of the mixture is highly sensitive to the compressibility of the entrained air, the effect of the entrained air is examined at two pressures, one at ambient representing the lower limit of pressure, and one at 4 atmospheres representing a typical line pressure in a paper process. As shown, the consistency of the liquid slurry 12, i.e., the pulp content, has little effect on the relationship between entrained air volume fraction and mixture sound speed. This indicates that an entrained air measurement could be accurately performed, within 0.01% or so, with little or no knowledge of the consistency of the slurry. The chart does show a strong dependence on line pressure. Physically, this effect is linked to the compressibility of the air, and thus, this indicates that reasonable estimates of line pressure and temperature would be required to accurately interpret mixture sound speed in terms of entrained air gas volume fraction.

FIG. 7 also shows that for the region of interest, from roughly 1% entrained air to roughly 5% entrained air, mixture sound speeds ($a_{mix}$) are quite low compare to the liquid-only sound speeds. In this example, the sound speed of the pure water and the 5% pulp slurry were calculated, based on reasonable estimates of the constituent densities and compressibilities, to be 1524 m/s and 1541 m/s, respectively. The sound speed of these mixtures with 1% to 5% entrained air at typical operating pressure (1 atm to 4 atms) are on the order of 100 m/sec. The implication of these low sound speed is that the mixture sound speed could be accurately determined with a array of sensors, ie using the methodology described in aforementioned U.S. patent application Ser. No. 10/007,749, with an aperture that is similar, or identical, to an array of sensors that would be suitable to determine the convection velocity, using the methodology described in aforementioned U.S. patent application Ser. No. 10/007,736 which is incorporated herein by reference.

For the sound speed measurement, the apparatus 1–10 utilizes array processing algorithms. The temporal and spatial frequency content of sound propagating within the process piping is related through a dispersion relationship.

$$k = \frac{\omega}{a_{mix}}$$

As before, k is the wave number, defined as $k=2\pi/\lambda$, $\omega$ is the temporal frequency in rad/sec, and $a_{mix}$ is the speed at which sound propagates within the process piping. Unlike disturbances, which convect with the flow, however, sound generally propagates in both directions, with and against the mean flow. For these cases, the acoustic power is located along two acoustic ridges, one for the sound traveling with the flow at a speed of $a_{mix}+V_{mix}$ and one for the sound traveling against the flow at a speed of $a_{mix}-V_{mix}$. FIG. 9 shows a k-$\omega$ plot generated for acoustic sound field recorded from water flowing at a rate of 240 gpm containing ~2% entrained air by volume in a 3 in, schedule 10, stainless steel pipe. The k-$\omega$ plot was constructed using data from an array of strain-based sensors attached to the outside of the pipe. Two acoustic ridges are clearly evident. Based on the slopes of the acoustic ridges, the sound speed for this for this mixture was 330 ft/sec (100 m/s), consistent with that predicted by the Wood equation. Note that adding 2% air by volume reduces the sound speed of the bubbly mixture to less than 10% of the sound speed of single phase water.

In one embodiment of the present invention as shown in FIG. 1, each of the pressure sensors 18–21 may include a piezoelectric film sensor to measure the unsteady pressures of the mixture 12 using either technique described hereinbefore.

The piezoelectric film sensors include a piezoelectric material or film to generate an electrical signal proportional to the degree that the material is mechanically deformed or stressed. The piezoelectric sensing element is typically conformed to allow complete or nearly complete circumferential measurement of induced strain to provide a circumferential-averaged pressure signal. The sensors can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc.

Piezoelectric film ("piezofilm"), like piezoelectric material, is a dynamic material that develops an electrical charge proportional to a change in mechanical stress. Consequently, the piezoelectric material measures the strain induced within the pipe 14 due to unsteady pressure variations (e.g., vortical and/or acoustical) within the process mixture 12. Strain within the pipe is transduced to an output voltage or current by the attached piezoelectric sensor. The piezoelectrical material or film may be formed of a polymer, such as polarized fluoropolymer, polyvinylidene fluoride (PVDF). The piezoelectric film sensors are similar to that described in U.S. patent application Ser. No. 10/712,833, which is incorporated herein by reference.

Another embodiment of the present invention include a pressure sensor such as pipe strain sensors, accelerometers, velocity sensors or displacement sensors, discussed hereinafter, that are mounted onto a strap to enable the pressure sensor to be clamped onto the pipe. The sensors may be removable or permanently attached via known mechanical techniques such as mechanical fastener, spring loaded, clamped, clam shell arrangement, strapping or other equivalents. These certain types of pressure sensors, it may be desirable for the pipe 12 to exhibit a certain amount of pipe compliance.

Instead of single point pressure sensors 18–21, at the axial locations along the pipe 12, two or more pressure sensors may be used around the circumference of the pipe 12 at each of the axial locations. The signals from the pressure sensors around the circumference at a given axial location may be averaged to provide a cross-sectional (or circumference) averaged unsteady acoustic pressure measurement. Other numbers of acoustic pressure sensors and annular spacing may be used. Averaging multiple annular pressure sensors reduces noises from disturbances and pipe vibrations and other sources of noise not related to the one-dimensional acoustic pressure waves in the pipe 12, thereby creating a spatial array of pressure sensors to help characterize the one-dimensional sound field within the pipe 12.

The pressure sensors 18–21 of FIG. 1 described herein may be any type of pressure sensor, capable of measuring the unsteady (or ac or dynamic) pressures within a pipe 14, such as piezoelectric, optical, capacitive, resistive (e.g., Wheatstone bridge), accelerometers (or geophones), velocity measuring devices, displacement measuring devices, etc. If optical pressure sensors are used, the sensors 18–21 may be Bragg grating based pressure sensors, such as that described in U.S. patent application Ser. No. 08/925,598, entitled "High Sensitivity Fiber Optic Pressure Sensor For Use In Harsh Environments", filed Sep. 8, 1997, now U.S. Pat. No. 6,016,702, and in U.S. patent application Ser. No. 10/224,821, entitled "Non-Intrusive Fiber Optic Pressure Sensor for Measuring Unsteady Pressures within a Pipe", which are incorporated herein by reference. In an embodiment of the present invention that utilizes fiber optics as the pressure sensors 14 they may be connected individually or may be multiplexed along one or more optical fibers using wavelength division multiplexing (WDM), time division multiplexing (TDM), or any other optical multiplexing techniques.

In certain embodiments of the present invention, a piezoelectronic pressure transducer may be used as one or more of the pressure sensors 15–18 and it may measure the unsteady (or dynamic or ac) pressure variations inside the tube 14 by measuring the pressure levels inside of the tube. These sensors may be ported within the pipe to make direct contact with the mixture 12. In an embodiment of the present invention, the sensors 14 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

It is also within the scope of the present invention that any strain sensing technique may be used to measure the variations in strain in the pipe, such as highly sensitive piezoelectric, electronic or electric, strain gages and piezo-resistive strain gages attached to the pipe 12. Other strain gages include resistive foil type gages having a race track configuration similar to that disclosed U.S. patent application Ser. No. 09/344,094, filed Jun. 25, 1999, now U.S. Pat. No. 6,354,147, which is incorporated herein by reference. The invention also contemplates strain gages being disposed about a predetermined portion of the circumference of pipe 12. The axial placement of and separation distance $\Delta X_1$, $\Delta X_2$ between the strain sensors are determined as described herein above.

It is also within the scope of the present invention that any other strain sensing technique may be used to measure the variations in strain in the tube, such as highly sensitive piezoelectric, electronic or electric, strain gages attached to or embedded in the tube 14.

While a number of sensor have been described, one will appreciate that any sensor the measures the speed of sound propagating through the fluid may be used with the present invention, including ultrasonic sensors.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. An apparatus for measuring the gas volume fraction process flow flowing within a pipe, the apparatus comprising:

at least two sensors that provide a sound measurement signal indicative of sound waves propagating in the process flow flowing within the pipe; and a processor that determines the slope of an acoustic ridge in the k-ω plane, in response to the sound measurement signals, to provide a sound speed signal indicative of the speed of sound propagating through the process flow, and that determines the gas volume fraction of the flow, in response to the sound speed signal.

2. The apparatus of claim 1, wherein the at least two sensors include at least two pressure strain sensors at different axial locations along the pipe, each of the pressure strain sensors providing a respective strain signal indicative of an acoustic pressure disturbance within the pipe at a corresponding axial position.

3. The apparatus of claim 2, wherein the strain sensors are pressure sensors.

4. The apparatus of claim 1, wherein the process flow is one of a liquid having entrained gas, a mixture having entrained gas, and a slurry having entrained gas.

5. The apparatus of claim 1, wherein the processor determines the gas volume fraction using at least one of the pressure and temperature of the process flow.

6. The apparatus of claim 5, wherein the apparatus further includes a least one of a pressure sensor and temperature sensor to respective determine the pressure and temperature of the process flow.

7. The apparatus of claim 1, wherein the sound waves are one dimensional acoustic waves.

8. The apparatus of claim 1, wherein the at least two sensors include 3, 4, 5, 6, 7, 8, 9, 10, 11, 12, 13, 14, 15, or 16 sensors.

9. The apparatus of claim 1, further includes an acoustic source for generating sound waves within the process flow.

10. The apparatus of claim 1, wherein the sound wave is a passive noise.

11. The apparatus of claim 1, wherein the gas volume fraction is determined using the following formula:

Gas Voulume Fraction = $-B+\sqrt{B^2-4*A*C})/(2*A)$ wherein $A=1+rg/rl*(K_{eff}/P-1)K_{eff}P$, $B=K_{eff}P-2+rg/rl$; $C=1-K_{eff}/rl*a_{meas}^2$; Rg=gas density, rl=liquid density, $K_{eff}$=effective K (modulus of the liquid and pipewall), P=pressure, and $a_{meas}$=measured speed of sound.

12. A method of measuring the gas volume fraction process flow flowing within a pipe, the method comprising:

measuring the sound waves propagating in the process flow flowing within the pipe to provide a sound measurement signal;

determining the slope of an acoustic ridge in the k-ω plane, in response to the sound measurement signals, to provide a sound speed signal indicative of the speed of sound propagating through the process flow, and determining the gas volume fraction of the process flow, in response to the sound speed signal.

13. The method of claim 12 further comprises providing a least two sensors that measure the sound waves propagating in the process flow.

14. The method of claim 13, wherein the at least two strain sensors are at different axial locations along the pipe, each of the strain sensors providing a respective strain signal indicative of an a acoustic pressure disturbance within the pipe at a corresponding axial position.

15. The method of claim 12, wherein the process flow is one of a liquid having entrained gas, a mixture having entrained gas, and a slurry having entrained gas.

16. The method of claim 12, wherein the processor determines the gas volume fraction using at least one of the pressure and temperature of the process flow.

17. The method of claim 16, wherein the apparatus further includes at least one of a pressure sensor and temperature sensor to respective determine the pressure and temperature of the process flow.

18. The method of claim 12, wherein the at least two sensors include 3, 4, 5, 6, 7, 8, 9, 10, 11, 12, 13, 14, 15, or 16 sensors.

19. The method of claim 12, further includes an acoustic source for generating sound waves within the process flow.

20. The method of claim 12, wherein the gas volume fraction is determined using the following formula:

Gas Voulume Fraction=$-B+\sqrt{B^2-4*A*C})/(2*A)$ wherein $A=1+rg/rl*(K_{eff}/P-1)-K_{eff}/P$, $B=K_{eff}P-2+rg/rl$; $C=1-K_{eff}/rl*a_{meas}^2$; Rg=gas density, rl=liquid density, $K_{err}$=effective K (modulus of the liquid and pipewall), P=pressure, and $a_{meas}$=measured speed of sound.

* * * * *